(12) United States Patent
Jayaraman et al.

(10) Patent No.: US 12,030,948 B2
(45) Date of Patent: Jul. 9, 2024

(54) ANTIBODY FORMULATION

(71) Applicant: DR. REDDY'S LABORATORIES LIMITED, Hyderabad (IN)

(72) Inventors: Murali Jayaraman, Kancheepuram (IN); Anuja Chandrasekar, Chennai (IN)

(73) Assignee: DR. REDDY'S LABORATORIES LIMITED, Hyderabad (IN)

( * ) Notice: Subject to any disclaimer, the term of this patent is extended or adjusted under 35 U.S.C. 154(b) by 911 days.

(21) Appl. No.: 17/045,380

(22) PCT Filed: Apr. 10, 2019

(86) PCT No.: PCT/IN2019/050292
§ 371 (c)(1),
(2) Date: Oct. 5, 2020

(87) PCT Pub. No.: WO2019/198100
PCT Pub. Date: Oct. 17, 2019

(65) Prior Publication Data
US 2021/0147555 A1    May 20, 2021

(30) Foreign Application Priority Data

Apr. 10, 2018   (IN) ............................ 201841013646

(51) Int. Cl.
*C07K 16/28* (2006.01)
*A61K 47/18* (2017.01)
*A61K 47/26* (2006.01)

(52) U.S. Cl.
CPC .......... *C07K 16/2839* (2013.01); *A61K 47/18* (2013.01); *A61K 47/26* (2013.01)

(58) Field of Classification Search
CPC ................................................ C07K 16/2839
See application file for complete search history.

(56) References Cited

U.S. PATENT DOCUMENTS

| | | | |
|---|---|---|---|
| 9,764,033 B2 | 9/2017 | Diluzio et al. | |
| 2009/0208492 A1* | 8/2009 | O'Connor | C07K 16/2839 424/133.1 |
| 2012/0282249 A1* | 11/2012 | Fox | A61P 1/00 424/133.1 |

FOREIGN PATENT DOCUMENTS

| | | | | |
|---|---|---|---|---|
| WO | WO-2004071439 A2 * | 8/2004 | ........... | A61K 39/395 |
| WO | WO-2006044908 A2 * | 4/2006 | ......... | A61K 31/7012 |
| WO | 2012/076670 A2 | 6/2012 | | |
| WO | WO-2017015198 A1 * | 1/2017 | ....... | A61K 39/39591 |
| WO | WO-2020104705 A2 * | 5/2020 | ........... | C07K 16/241 |

OTHER PUBLICATIONS

Sule et al (Molecular Pharmaceutics, 2012, vol. 9, pp. 744-751) (Year: 2012).*
International Search Report dated Jul. 18, 2019, for corresponding International Patent Application No. PCT/IN2019/050292.
Written Opinion dated Jul. 18, 2019, for corresponding International Patent Application No. PCT/IN2019/050292.

* cited by examiner

*Primary Examiner* — Karen A. Canella
(74) *Attorney, Agent, or Firm* — Pergament & Cepeda LLP; Milagros A. Cepeda; Edward D. Pergament

(57) ABSTRACT

The present invention discloses a stable pharmaceutical formulation of an antibody, wherein the formulation contains buffer, surfactant, sugar, and optionally contains a free amino acid. The disclosed formulation is stable at 50° C. for two weeks. In addition, the formulation maintains at least 96% of the antibody in monomeric form under above said storage conditions.

6 Claims, 8 Drawing Sheets

ANTIBODY FORMULATION

This application is a National Stage Application under 35 U.S.C. § 371 of PCT International Application No. PCT/IN2019/050292, filed Apr. 10, 2019, which claims the benefit of Indian provisional patent application No. 201841013646 filed on Apr. 10, 2018; all of which are herein incorporated by reference in their entireties.

FIELD OF INVENTION

The present invention is related to stable formulations of an antibody molecule. The disclosed formulations are compatible with lyophilized as well as liquid form and also suitable for intravenous and/or subcutaneous route of administration.

BACKGROUND

Over the past two decades, recombinant DNA technology has led to the commercialization of many proteins, particularly antibody therapeutics. The effectiveness of these therapeutic antibodies is majorly dependent on the stability, route of administration and their dosage forms and concentrations. This in turn, necessitates therapeutic antibodies to be formulated appropriately to retain the stability and activity of a therapeutic antibody.

Formulations for each route of administration and dosage forms may be unique and, therefore, have specific requirements. Solid dosage forms, such as lyophilized powders, are generally more stable than liquid (aqueous) formulations. However, reconstitution of the lyophilized formulation requires a significant vial overfill, care in handling and involves high production cost relative to a liquid formulation. While liquid formulations are advantageous in these and are usually preferred for injectable protein therapeutics (in terms of convenience for the end user and ease of preparation for the manufacturer), this form may not always be feasible given the susceptibility of proteins to denaturation, aggregation and oxidation under stresses such as temperature, pH changes, agitation etc. All of these stress factors could result in the loss of biological activity of a therapeutic protein/antibody. In particular, high concentration liquid formulations are susceptible to degradation and/or aggregation. Nevertheless, high concentration formulations may be desirable for subcutaneous or intravenous route of administration, as the frequency of administration and injection volume is reduced. On the other hand, specific treatment schedule and dosing might require a low concentration formulation and prefer intravenous route of administration for more predictable delivery and complete bioavailability of the therapeutic drug.

Hence, designing a formulation that is stable at high or low concentrations of the therapeutic protein/antibody, aiding in different route of administration (intravenous or subcutaneous) and which is suitable in lyophilized or liquid form, pose a significant developmental challenge.

Further, every protein or antibody with its unique characteristics and properties of degradation, adds to the complexity in the development of a stable formulation and may demand a specific formulation.

A stable formulation of a therapeutic protein or antibody involves addition of a wide variety of stabilizers/excipients including amino acids, sugars, polyols, surfactants, salts, polymers, amines, anti-oxidants, chelators etc. Many of the FDA approved therapeutic proteins/antibodies contain more than one category of stabilizers.

A formulation combination with increased concentration of protein and/or stabilizers may increase the viscosity of the formulation, in turn increasing the injection time and pain at the site of injection and also pose difficulties during processing of the drug substance. Hence, it is necessary to develop an improved formulation, in lyophilized as well as liquid form which contains minimal number or concentration of excipients, yet stabilizing the drug at a wide range of its concentration.

SUMMARY

The present invention discloses a stable pharmaceutical formulation of an antibody comprising buffer, sugar and surfactant. The antibody according to the invention binds to $\alpha 4\beta 7$. The disclosed $\alpha 4\beta 7$ antibody formulation is stable at 50° C. for two weeks and change in aggregate and fragment content of the antibody in the formulation is less than about 1.5% under above mentioned storage conditions. Further, the concentration of sugar is less than 80 mg/ml, preferably less than 70 mg/ml. The formulation optionally contains free amino acids which act as stabilizers.

The invention discloses a stable pharmaceutical formulation of $\alpha 4\beta 7$ antibody comprising buffer, sugar, free amino acid and surfactant. The disclosed $\alpha 4\beta 7$ antibody formulation is stable at 50° C. for two weeks. Further, the change in aggregate and fragment content of the antibody in the formulation is less than 1% at 50° C. for two weeks.

In particular, the invention discloses a combination of optimum and yet lower concentrations of excipients, viz., sugar and free amino acid, in $\alpha 4\beta 7$ antibody formulation. The excipients of the disclosed formulation controls the change in aggregate and fragment content under accelerated conditions and in addition maintains the main peak content.

BRIEF DESCRIPTION OF DRAWINGS

FIG. 1(a) represents LMW content, FIG. 1(b) represents aggregate content and FIG. 1(c) represents monomer content during storage conditions at 50° C. for two weeks.

FIG. 3(a) represents LMW content, FIG. 3(b) represents aggregate content and FIG. 3(c) represents monomer content during storage conditions at 50° C. for two weeks.

FIG. 5(a) represents LMW content, FIG. 5(b) represents aggregate content and FIG. 5(c) represents monomer content during storage conditions at 50° C. for two weeks.

FIG. 7(*a*) represents LMW content, FIG. 7(*b*) represents aggregate content and FIG. 7(*c*) represents monomer content during storage conditions at 50° C. for two weeks.

DETAILED DESCRIPTION OF THE INVENTION

Definitions

Figure 1:
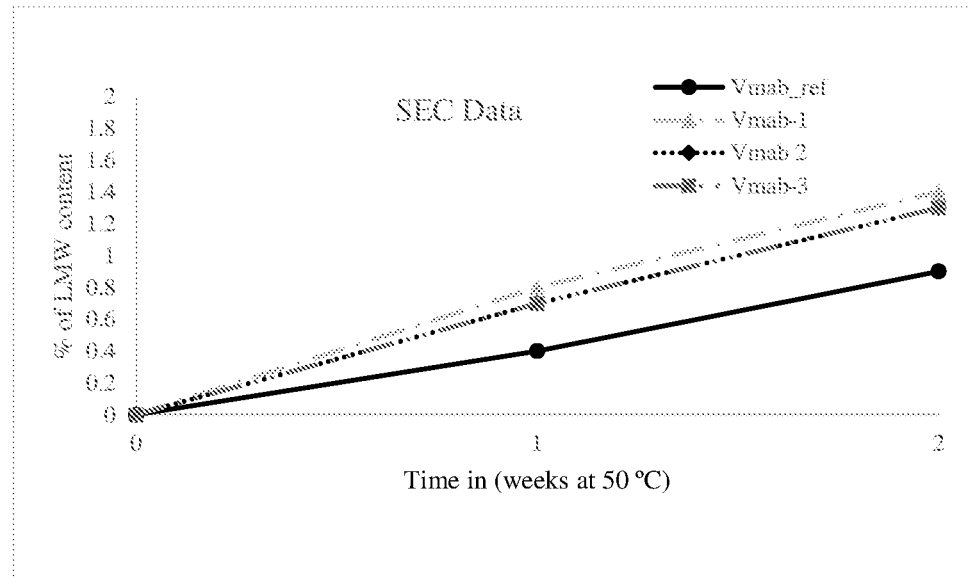
FIG. 1 illustrates the effect of various sugars on the LMW, HMW and monomer content of vedolizumab (60 mg/ml) formulations prepared as per example and analyzed using SEC chromatography.
Figure 1:
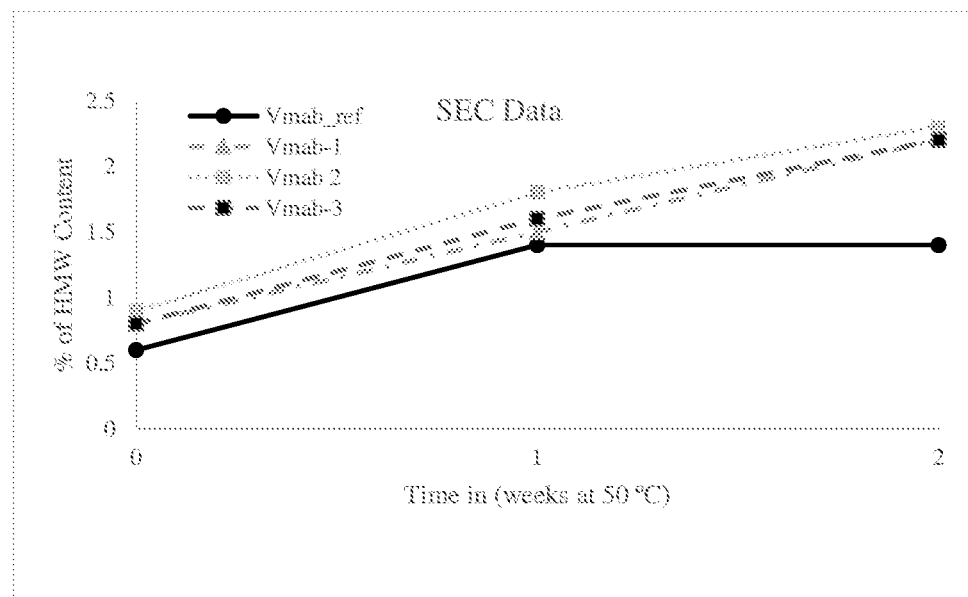
Figure 1:
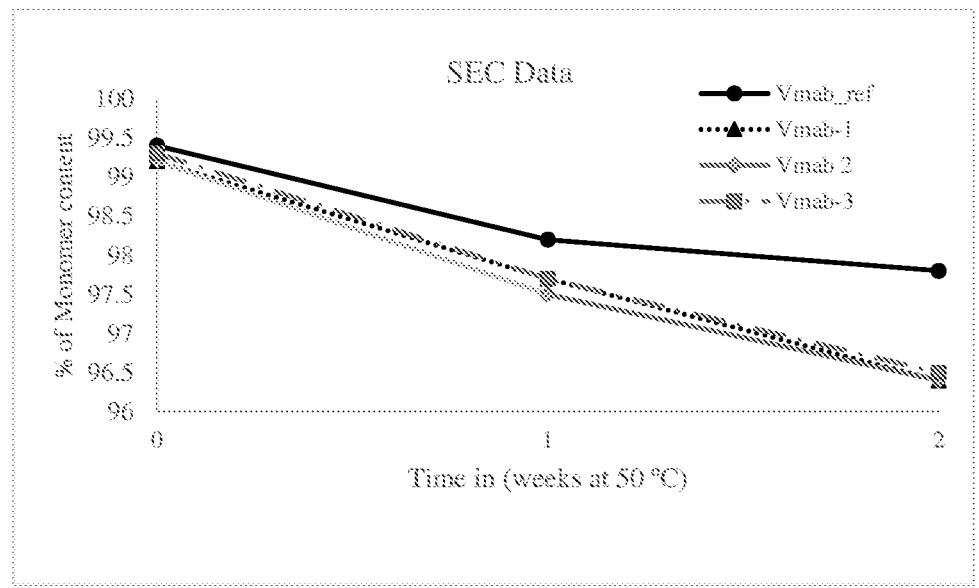

The term "antibody" refers to a glycoprotein comprising at least two heavy (H) chains and two light (L) chains inter-connected by disulfide bonds, or an antigen-binding portion thereof. The "antibody" as used herein encompasses whole antibodies or any antigen binding fragment (i.e., "antigen-binding portion") or fusion protein thereof.

The term "stable" formulation refers to the formulation wherein the antibody therein retains its physical stability and/or chemical stability and/or biological activity, upon storage.

Stability studies provides evidence of the quality of an antibody under the influence of various environmental factors during the course of time. ICH's "Q1A: Stability Testing of New Drug Substances and Products," states that data from accelerated stability studies can be used to evaluate the effect of short-term excursions higher or lower than label storage conditions that may occur during the shipping of the antibodies.

Various analytical methods are available for measuring the physical and chemical degradation of the antibody in the pharmaceutical formulations. An antibody "retains its physical stability" in a pharmaceutical formulation if it shows substantially no signs of aggregation, precipitation and/or denaturation upon visual examination of color and/or clarity, or as measured by UV light scattering or by size exclusion chromatography. An antibody is said to "retain its chemical stability" in a pharmaceutical formulation when its shows no or minimal formation of product variants which may include variants as a result of chemical modification of antibody of interest such as deamination, oxidation etc. Analytical methods such as ion exchange chromatography and hydrophobic ion chromatography may be used to investigate the chemical product variants.

The term 'monomer' as used herein describes antibodies consisting of two light chains and two heavy chains. The monomer content of an antibody composition is typically analyzed by size exclusion chromatography (SEC). As per the separation principle of SEC the large molecules or molecules with high molecular weight (HMW) elute first followed by smaller or lower weight molecules. In a typical SEC profile for an antibody composition, aggregates that may include dimers, multimers, etc., elute first, followed by monomer, and the clipped antibody variants or degradants may be eluted last. In some circumstances the aggregate peak or the degradant peaks may not elute as a baseline separated peaks but instead as a shoulder or abnormal broad peaks. In order to maintain the appropriate activity of an antibody, in particular of a therapeutic antibody, it is desirable to reduce the formation of aggregate or fragmentation of products and hence control the monomer content to a target value. Ability to inhibit the formation of aggregate and degradant content as measured at various time points during stability studies may indicate the suitability of the candidate formulation for antibody of interest. TSK-GEL G3000SWXL (7.8 mm×30 cm) column from TOSCH can be used on water HPLC to perform SEC.

The term 'main peak' as used herein refers to the peak that elutes in abundance (major peak) during a cation exchange chromatography. The peak that elutes earlier than the main peak, during a cation exchange chromatography, with a charge that is acidic relative to the main peak, is termed acidic variant peak. The peak that elutes later than the main peak, during a cation exchange chromatography, with a charge that is relatively basic than the main peak, is termed as basic variant peak. The main peak content can be determined by Ion exchange chromatography (IEC). There are two modes of IEC available viz., cation and anion exchange chromatography. Positively charged molecules bind to anion exchange resins while negatively charged molecules bind to cation exchange resins. In a typical cation exchange chromatographic profile of an antibody composition acidic variants elute first followed by the main peak and thereafter lastly the basic variants will be eluted. The acidic variants are a result of antibody modifications such as deamidation of asparagine residues. The basic variants are a result of incomplete removal of C-terminal lysine residue(s). In general, in an antibody a lysine residue is present at the C-terminal end of both heavy and light chain. An antibody molecule containing lysine at both heavy and light chain is referred to as K2 variant, the antibody molecule containing lysine residue at either one of heavy and light chain is referred to as K1 variant and antibody molecule having none is K0 molecule. Carboxypeptidase B (CP-B enzyme) enzyme acts on the C-terminal lysine residues present on K2 and K1 variants and thus converting them as K0 molecules. As per circumstances of the case, the IEC analysis can be carried out for samples digested with carboxypeptidase B (CP-B) enzyme. In a typical stability study it is expected that a stable formulation leads to reduction in formation of charge variants (acidic and basic variants), during the study, and hence minimize any reduction in main peak content.

The term "free amino acid" as used herein refers to amino acid that is included in the formulation and is not a part of the buffer component. An amino acid may be present in its D- and/or L-form. The amino acid may be present as any suitable salt e.g. a hydrochloride salt, such as Arginine-HCl.

Examples of salts include, but not limited to, sodium chloride, potassium chloride, magnesium chloride, sodium thiocyanate, ammonium thiocyanate, ammonium sulfate, ammonium chloride, calcium chloride, zinc chloride and/or sodium acetate.

Pharmaceutically acceptable excipients refer to the additives or carriers, which may contribute to stability of the antibody in formulation. The excipients may encompass stabilizers and tonicity modifiers. Examples of stabilizers and tonicity modifiers include, but not limited to, sugars, polyols, salts, surfactants, and derivatives and combination thereof.

Sugar/s herein includes sugars and sugar alcohols such as polyols. Sugars can be referred to monosaccharides, disaccharides, and polysaccharides. Examples of sugars include, but are not limited to, sucrose, trehalose, glucose, dextrose, raffinose and others. Examples of polyols include, but are not limited to, mannitol, sorbitol, and others.

Surfactant refers to pharmaceutically acceptable excipients used to protect the protein formulations against various stress conditions, like agitation, shearing, exposure to high temperature etc. The suitable surfactants include but are not limited to polyoxyethylensorbitan fatty acid esters such as Tween 20™ or Tween 80™, polyoxyethylene-polyoxypropylene copolymer (e.g. Poloxamer, Pluronic), sodium dodecyl sulphate (SDS) and the like or combination thereof.

Certain specific aspects and embodiments of the invention are more fully described by reference to the following examples. However, these examples should not be construed as limiting the scope of the invention in any manner.

DETAILED DESCRIPTION OF THE EMBODIMENTS

The present invention discloses, a stable pharmaceutical formulation of an antibody comprising buffer, sugar and surfactant.

In the above embodiment, the antibody is a therapeutic monoclonal antibody.

In the above mentioned embodiment, the therapeutic antibody binds to $\alpha 4\beta 7$.

In one embodiment the invention discloses, a stable pharmaceutical formulation of $\alpha 4\beta 7$ antibody comprising buffer, sugar and surfactant wherein the concentration of sugar is less than 80 mg/ml, preferably less than 70 mg/ml, more preferably 60 mg/ml.

In the above said embodiment, sugar present in the $\alpha 4\beta 7$ antibody formulation controls the formation of aggregates and fragments under storage conditions.

In the above said embodiment, the change in aggregate and fragment content of the $\alpha 4\beta 7$ antibody in the formulation is less than 1.5% at 50° C. for two weeks.

In any of the above said embodiment, the formulation optionally contains pharmaceutically acceptable excipients such as amino acids and salts.

In another embodiment, the invention discloses a stable $\alpha 4\beta 7$ antibody comprising buffer, sugar, free amino acid and surfactant.

In the above embodiment, the concentration of sugar is less than 70 mg/ml, preferably 30 mg/ml and the concentration of free amino acid is less than 15 mg/ml, preferably about 5 mg/ml which controls increase in aggregate and fragment content of the antibody in the formulation effectively.

In the above embodiment, the disclosed $\alpha 4\beta 7$ antibody formulation containing sugar and free amino acid is stable at 50° C. for two weeks and controls change in aggregate and fragment content of the antibody in the formulation to less than 1%.

In any of the above embodiments of the invention, buffer includes organic buffer, inorganic buffer and/or combination thereof.

In the above mentioned embodiment, the organic buffer includes histidine, succinate or acetate buffer and their salts thereof.

In yet another embodiment of the invention, the stable formulation of $\alpha 4\beta 7$ antibody comprises an inorganic buffer that includes, phosphate buffer.

In an embodiment, the invention discloses a stable pharmaceutical formulation of $\alpha 4\beta 7$ antibody comprising phosphate buffer, at least 60 mg/ml of sugar, 50 mM free amino acid, and surfactant, wherein the formulation is stable at 50° C. for two weeks and maintains at least 97% of the monomeric content of the antibody under above mentioned storage conditions.

In an embodiment, the invention discloses a stable pharmaceutical formulation of $\alpha 4\beta 7$ antibody comprising acetate buffer, at least 60 mg/ml of sugar, 50 mM free amino acid and surfactant, wherein the formulation is stable at 50° C. for two weeks and maintains at least 96% of monomeric content of the antibody. In addition, at least 55% of the antibody is maintained as main peak, in the disclosed formulation, under said storage conditions.

In an embodiment, the invention discloses a stable pharmaceutical formulation of $\alpha 4\beta 7$ antibody comprising succinate buffer, at least 60 mg/ml of sugar, 50 mM free amino acid, and surfactant, wherein the formulation is stable at 50° C. for two weeks and maintains at least 55% of the antibody is retained as main peak under said storage conditions.

In any of the above mentioned embodiments, the sugar is sucrose or trehalose or mannitol or sorbitol. Preferably, the sugar is trehalose.

In any of the above mentioned embodiments, the free amino acid is arginine or lysine or glycine or combinations or derivatives thereof.

In all of the above embodiments of the invention, the concentration of the $\alpha 4\beta 7$ antibody is about 50 mg/ml to about 200 mg/ml.

In any of the said embodiments of the invention, the pH of $\alpha 4\beta 7$ antibody formulation is from 6.0-7.0.

In an embodiment, the invention discloses $\alpha 4\beta 7$ antibody comprising buffer, sugar, free amino acid and surfactant, wherein the formulation is stable at 50° C. for two weeks.

In the above mentioned embodiment, the concentration of sugar is at least 30 mg/ml and less than 70 mg/ml, and preferably 60 mg/ml.

In the above said embodiment of the invention, the concentration of arginine is at least 5 mg/ml and less than 15 mg/ml, and preferably 10 mg/ml.

In any of the above mentioned embodiments, the formulation of $\alpha 4\beta 7$ antibody is a stable liquid (aqueous) formulation, which can be used for parenteral administration. Parenteral administration includes intravenous, subcutaneous, intra peritoneal, intramuscular administration or any other route of delivery generally considered to be falling under the scope of parenteral administration and as is well known to a skilled person.

In any of the above embodiments of the invention, the stable liquid/aqueous formulation is suitable and can be lyophilized as lyophilized powders. Further, the lyophilized formulation of $\alpha 4\beta 7$ antibody can be reconstituted with appropriate diluent to achieve the liquid formulation suitable for administration.

EXAMPLES

An $\alpha 4\beta 7$ antibody, vedolizumab, suitable for storage in the present pharmaceutical composition is produced by standard methods known in the art. For example, vedolizumab is prepared by recombinant expression of immunoglobulin light and heavy chain genes in a mammalian host cell such as Chinese Hamster Ovary cells. Further, the expressed vedolizumab is harvested and the crude harvest is subjected to standard downstream process steps that include purification, filtration and optionally dilution or concentration steps. For example, the crude harvest of vedolizumab may be purified using standard chromatography techniques such as affinity chromatography, ion-exchange chromatography and combinations thereof. The purified vedolizumab solution can additionally be subjected to one or more filtration steps, and the solution obtained is subjected to further formulation studies. Vedolizumab (at a concentration of 8 mg/ml) in Tris acetate buffer obtained from downstream chromatographic process was buffer exchanged and concentrated in histidine buffer up to 70 mg/ml. The concentrated vedolizumab was used in subsequent experiments.

Example 1

Stability of Vedolizumab in Presence of Various Sugars

Figure 2:
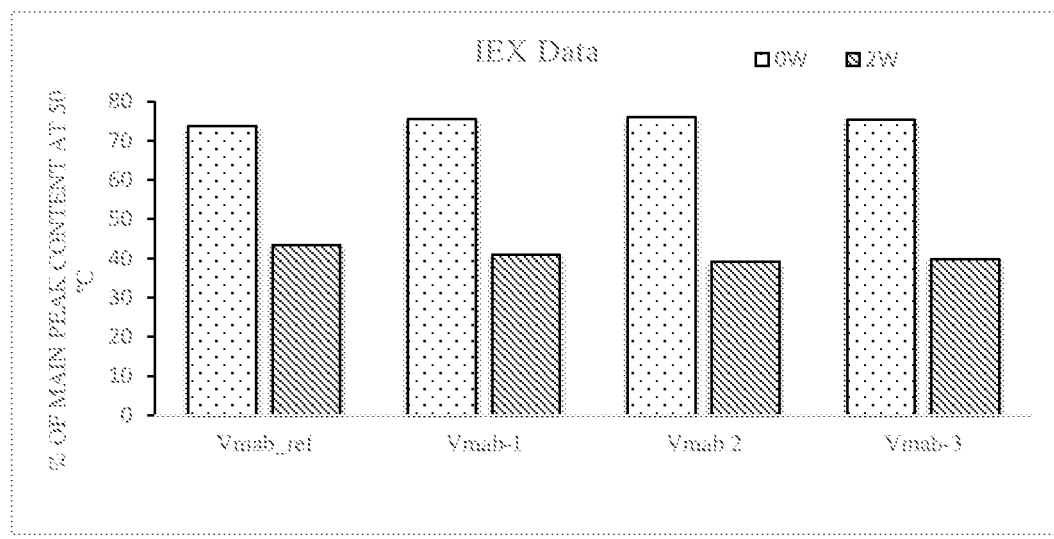
FIG. 2 illustrates the effect of various sugars on the main peak content of vedolizumab (60 mg/ml) formulations prepared as per example 1 and analyzed using IEX chromatography, after two weeks at 50° C.

To understand the effect of various sugars on the stability of vedolizumab, formulations with various sugars were prepared. A portion of the concentrated vedolizumab in histidine buffer background was buffer exchanged into 20 mM phosphate buffer. Further, excipients such as sugars and polysorbates were added to the formulations. FDA approved formulation of vedolizumab contains arginine, sucrose and polysorbate. Hence, the same excipients were added to vedolizumab in histidine buffer background and this has been used as reference standard in subsequent experiments. Details of the formulations are given in Table 1. All the samples were subjected for accelerated stability studies at 50° C. for two weeks. Post which, the samples were analysed for low molecular weight (LMW) or fragmented species, high molecular weight (HMW) species or aggregates and monomer content [results are shown in FIG. 1(a)-(c)] using size exclusion chromatography (SEC) and also checked for main peak content, using ion exchange chromatography [results are shown in FIG. 2]. Visual inspection data of the vedolizumab samples are given in Table 2.

TABLE 1

Compositions of vedolizumab formulations in presence of different sugars

| Sample Name | Composition |
| --- | --- |
| Vmab_Reference Standard (Vmab_ref) | Vedolizumab 60 mg/ml, 50 mM histidine buffer, monohydrochloride, 27.4 mg/mL L-arginine hydrochloride, 104.17 mg/mL sucrose, 0.6 mg/mL polysorbate 80 |
| Vmab_1 | Vedolizumab 60 mg/ml, 20 mM phosphate buffer, sucrose 30 mg/ml and 0.6 mg/mL polysorbate 80 |
| Vmab-2 | Vedolizumab 60 mg/ml, 20 mM phosphate buffer, sorbitol 30 mg/ml and 0.6 mg/mL polysorbate 80 |
| Vmab-3 | Vedolizumab 60 mg/ml, 20 mM phosphate buffer, trehalose 60 mg/ml and 0.6 mg/mL polysorbate 80 |

TABLE 2

Visual inspection data of vedolizumab (60 mg/ml) formulations prepared as per example 1

| Sample Name | Visual Inspection at 50° C. | | |
| --- | --- | --- | --- |
| | 0 W | 1 W | 2 W |
| Vmab_ref | Clear | Slightly Opalescent | Slightly Opalescent |
| Vmab_1 | Clear with few particles | Slightly Opalescent | Slightly Opalescent |
| Vmab-2 | Clear with few particles | Slightly Opalescent | Slightly Opalescent |
| Vmab-3 | Clear with few particles | Slightly Opalescent | Slightly Opalescent |

W—indicates weeks

Example 2

Formulations of Vedolizumab in Presence of Increased Concentration of Sucrose

To understand the effect of concentration of sucrose on the stability of vedolizumab, formulations with various concentrations of sucrose were prepared. A portion of the concentrated vedolizumab in histidine buffer background was buffer exchanged into 20 mM phosphate buffer. Post which, excipients such as sucrose, polysorbate, were added to vedolizumab present in histidine buffer background as well as phosphate buffer background.

Sucrose was added in increased concentrations to various vedolizumab samples to understand the effect of sucrose on protein stability.

Figure 3:
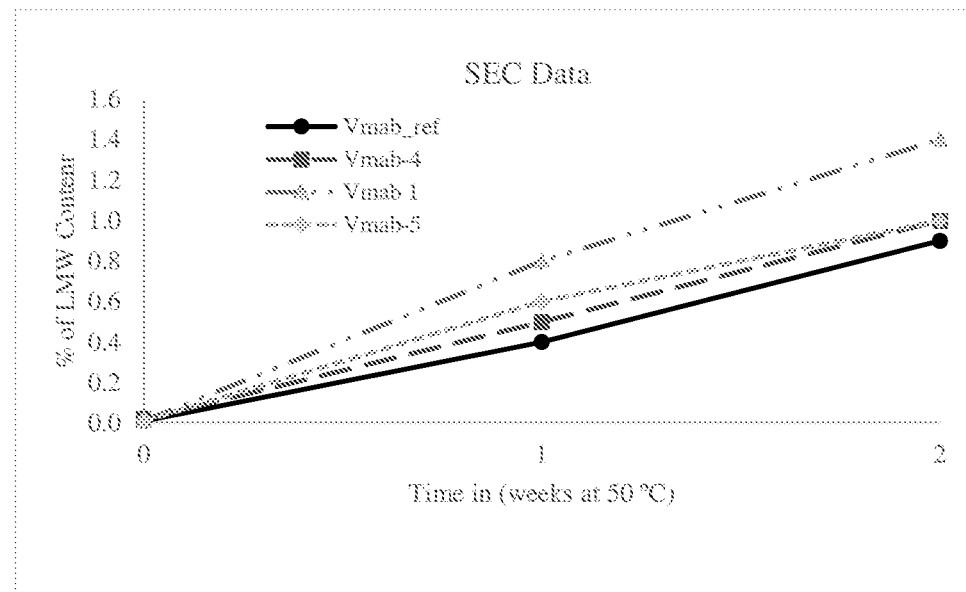
FIG. 3 illustrates the effect of increased concentration of sucrose on the LMW, HMW and monomer content of vedolizumab (60 mg/ml) formulations prepared as per example 2 and analyzed using SEC chromatography.
Figure 3:
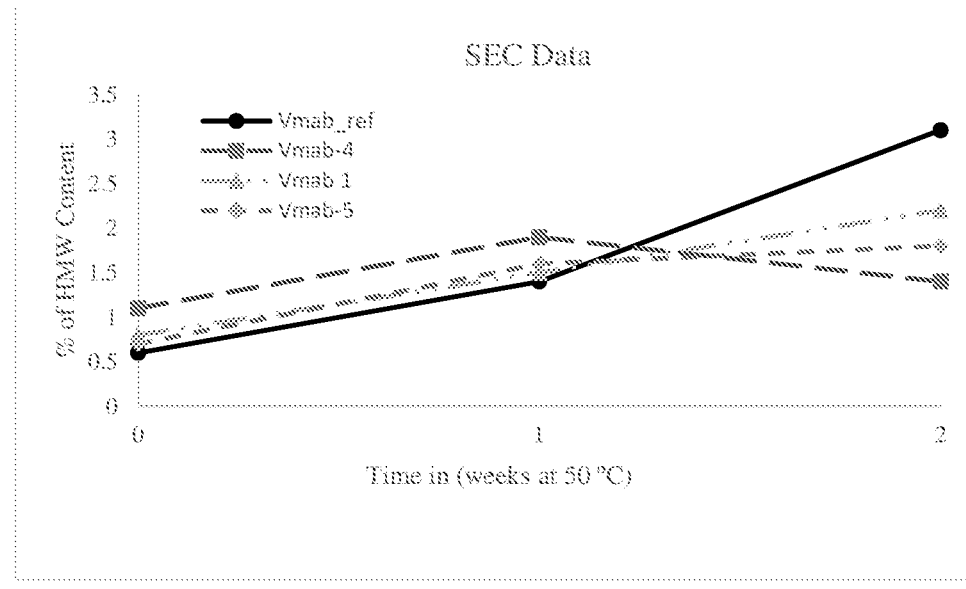
Figure 3:
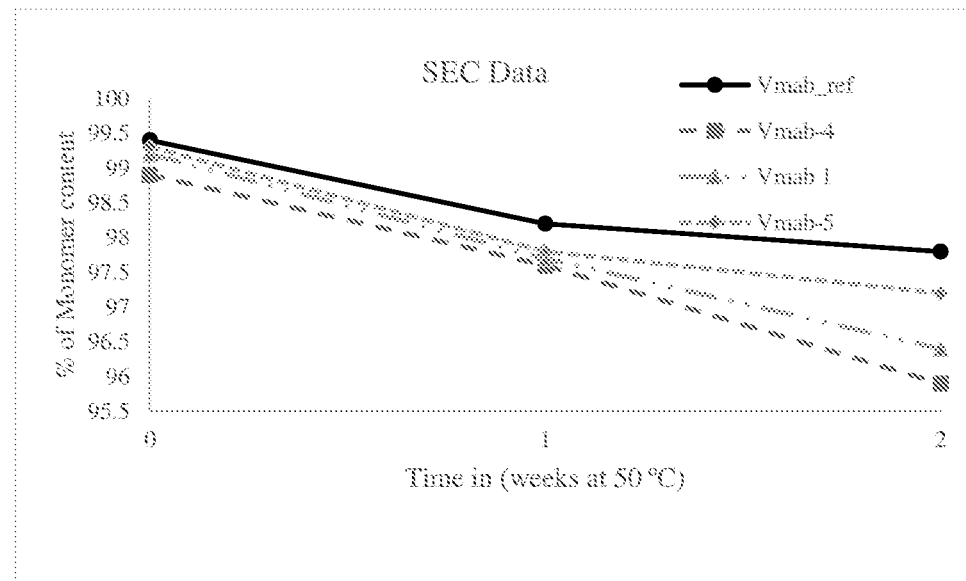
Figure 4:
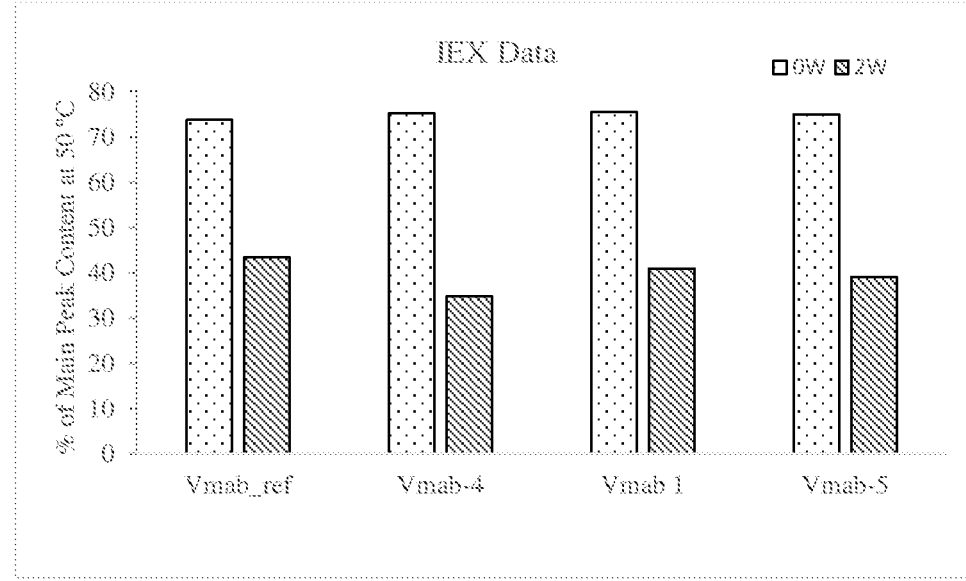
FIG. 4 illustrates the effect of increased concentration of sucrose on the main peak content of vedolizumab (60 mg/ml) formulations prepared as per example 2 and analyzed using IEX chromatography, after two weeks at 50° C.

Details of the formulations are given in Table 3. All the samples were subjected for stability studies at 50° C. for two weeks. Post which, the samples were analysed for low molecular weight (LMW/fragments) species, high molecular weight species (HMW/aggregates) and monomer content [results are shown in FIG. 3(a)-(c)] using size exclusion chromatography (SEC) and also checked for main peak content, using ion exchange chromatography [results are shown in FIG. 4]. Visual inspection data of the vedolizumab samples are given in Table 4.

TABLE 3

Compositions of vedolizumab formulations prepared as per example 2

| Sample Name | Composition |
| --- | --- |
| Vmab_ref | Vedolizumab 60 mg/ml, 50 mM histidine buffer, monohydrochloride, 27.4 mg/mL L-arginine hydrochloride, 104.17 mg/mL sucrose, 0.6 mg/mL polysorbate 80 |
| Vmab-4 | Vedolizumab 60 mg/ml, 20 mM phosphate buffer, sucrose 10 mg/ml and 0.6 mg/mL polysorbate 80 |
| Vmab-1 | Vedolizumab 60 mg/ml, 20 mM phosphate buffer, sucrose 30 mg/ml and 0.6 mg/mL polysorbate 80 |
| Vmab-5 | Vedolizumab 60 mg/ml, 20 mM phosphate buffer, sucrose 60 mg/ml and 0.6 mg/mL polysorbate 80 |

TABLE 4

Visual inspection data of vedolizumab (60 mg/ml) formulations prepared as per example 1

| Sample Name | Visual Inspection at 50° C. | | |
| --- | --- | --- | --- |
| | 0 W | 1 W | 2 W |
| Vmab_ref | Clear | Slightly Opalescent | Slightly Opalescent |
| Vmab_4 | Clear | Slightly Opalescent | Slightly Opalescent |
| Vmab-1 | Clear with few particles | Slightly Opalescent | Slightly Opalescent |
| Vmab-5 | Clear with few particles | Slightly Opalescent | Slightly Opalescent |

W—indicates weeks

Example 3

Formulations of Vedolizumab in Presence of Sugar and Amino Acid

Figure 5:
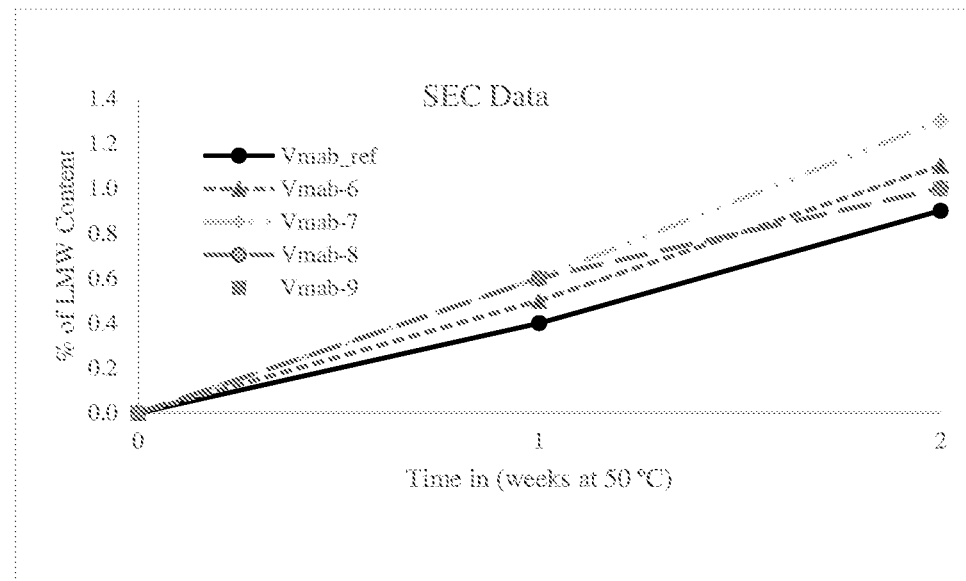
FIG. 5 illustrates the effect of amino acid and sugar concentration LMW, HMW and monomer content of vedolizumab (60 mg/ml) formulations prepared as per example 3 and analyzed using SEC chromatography.
Figure 5:
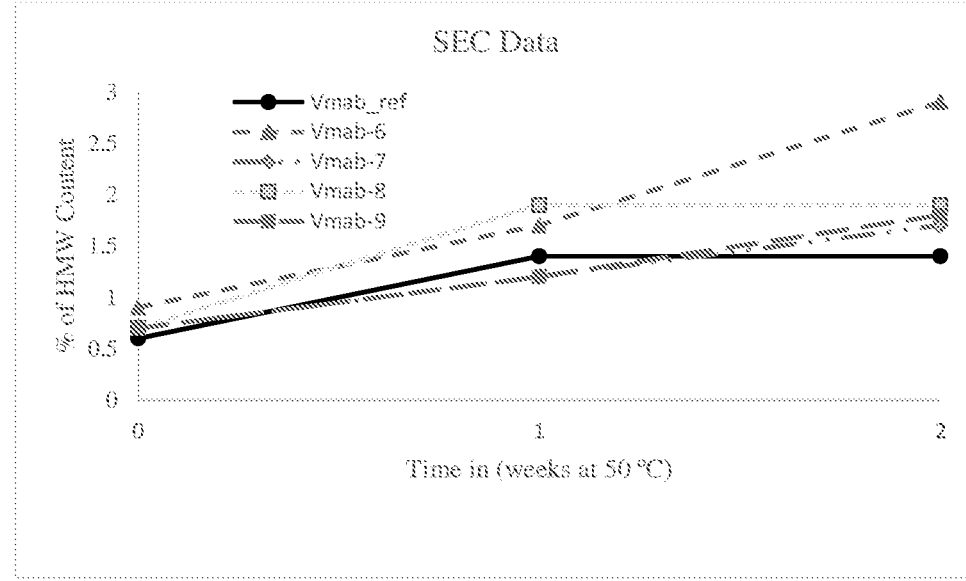
Figure 5:
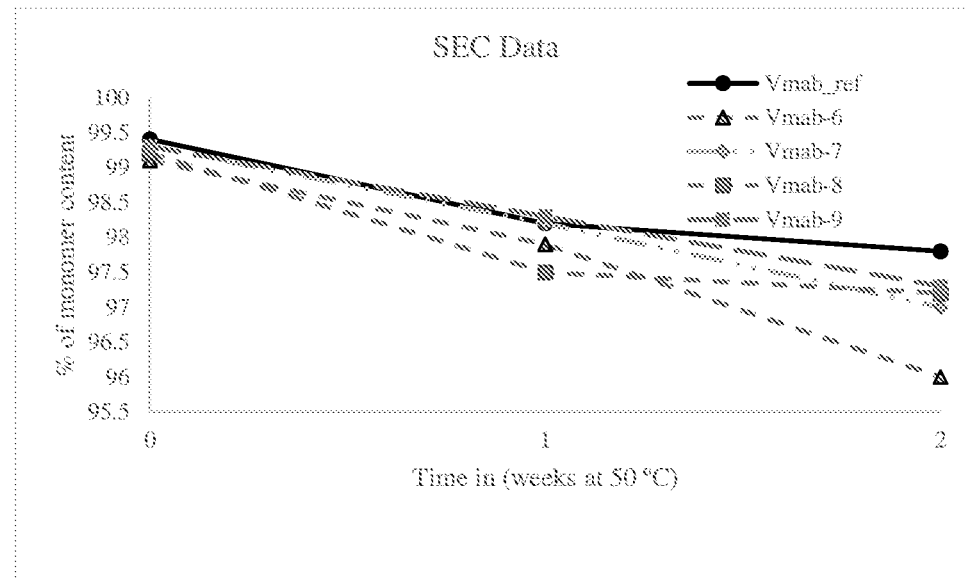
Figure 6:
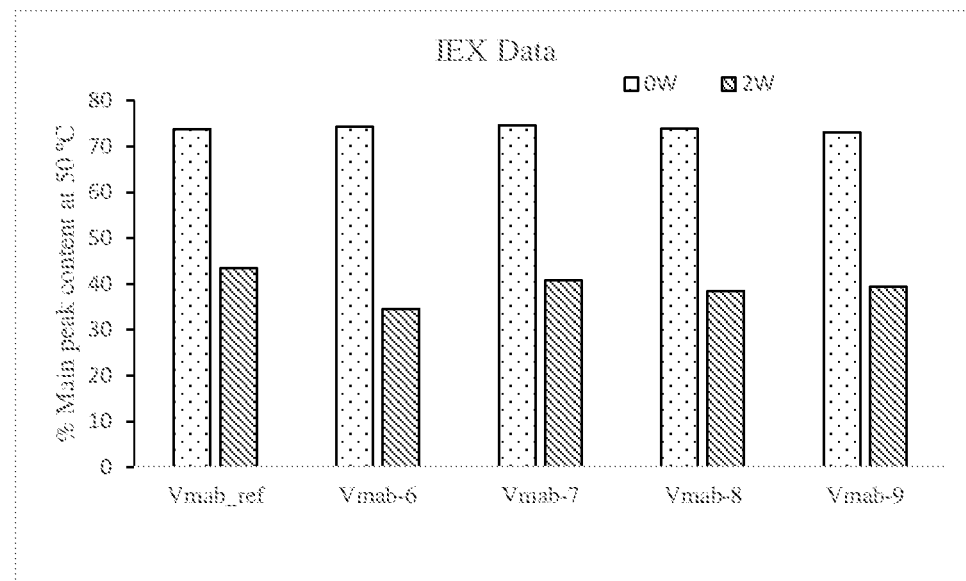
FIG. 6 illustrates the effect of amino acid and sugar concentration on the main peak content vedolizumab (60 mg/ml) formulations prepared as per example 3 and analyzed using IEX chromatography, after two weeks at 50° C.

To understand the effect of amino acid on the stability of vedolizumab, different concentrations of arginine were prepared and added to the formulations of example 2. Details of the formulation are given Table 5. All the samples were subjected for accelerated stability studies at 50° C. for two weeks. Post which, the samples were analyzed for aggregates, fragments and monomeric content of the antibody using size exclusion chromatography [results shown in FIG. 5(a)-(c)] using size exclusion chromatography (SEC) and also checked for main peak content using ion exchange chromatography [results shown in FIG. 6] and also for visual inspection [Table 6].

TABLE 5

Compositions of various vedolizumab formulations with free amino acid

| Sample Name | Composition |
|---|---|
| Vmab_ref | Vedolizumab 60 mg/ml, 50 mM histidine buffer, monohydrochloride, 27.4 mg/mL L-arginine hydrochloride, 104.17 mg/mL sucrose, 0.6 mg/mL polysorbate 80 |
| Vmab-6 | Vedolizumab 60 mg/ml, 20 mM phosphate buffer, sucrose 10 mg/ml and 0.6 mg/ml polysorbate 80, 5.3 mg/ml arginine |
| Vmab-7 | Vedolizumab 60 mg/ml, 20 mM phosphate buffer, sucrose 30 mg/ml and 0.6 mg/ml polysorbate 80, 5.3 mg/ml arginine |
| Vmab-8 | Vedolizumab 60 mg/ml, 20 mM phosphate buffer, sucrose 60 mg/ml and 0.6 mg/ml polysorbate 80, 5.3 mg/ml arginine |
| Vmab-9 | Vedolizumab 60 mg/ml, 20 mM phosphate buffer, sucrose 60 mg/ml and 0.6 mg/ml polysorbate 80, 10.5 mg/ml arginine |

TABLE 6

Visual inspection data of vedolizumab (60 mg/ml) formulations prepared as per example 3

| Sample Name | Visual Inspection at 50° C. | | |
|---|---|---|---|
| | 0 W | 1 W | 2 W |
| Vmab_ref | Clear | Slightly Opalescent | Slightly Opalescent |
| Vmab_6 | Clear | Slightly Opalescent | Slightly Opalescent |
| Vmab-7 | Clear with few particles | Slightly Opalescent | Opalescent |
| Vmab-8 | Slightly Opalescent | Opalescent | Slightly Opalescent |
| Vmab-9 | Slightly Opalescent | Slightly Opalescent | Slightly Opalescent |

W—indicates weeks

Example 4

Formulations of Vedolizumab in Various Buffer Backgrounds

Figure 7:
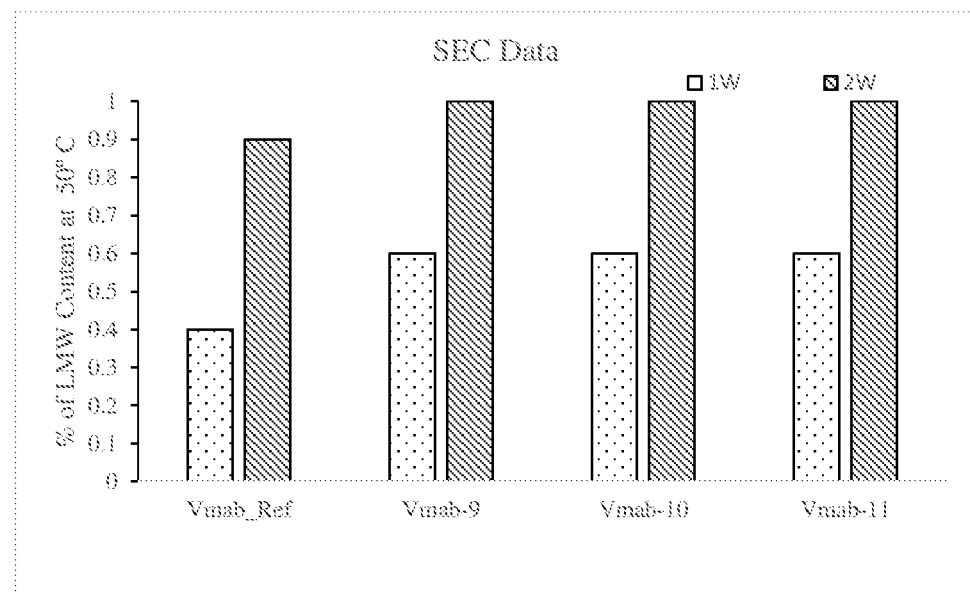
FIG. 7 illustrates the effect of buffer on LMW, HMW and monomer content of vedolizumab (60 mg/ml) formulations prepared as per example 4 and analyzed using SEC chromatography.
Figure 7:
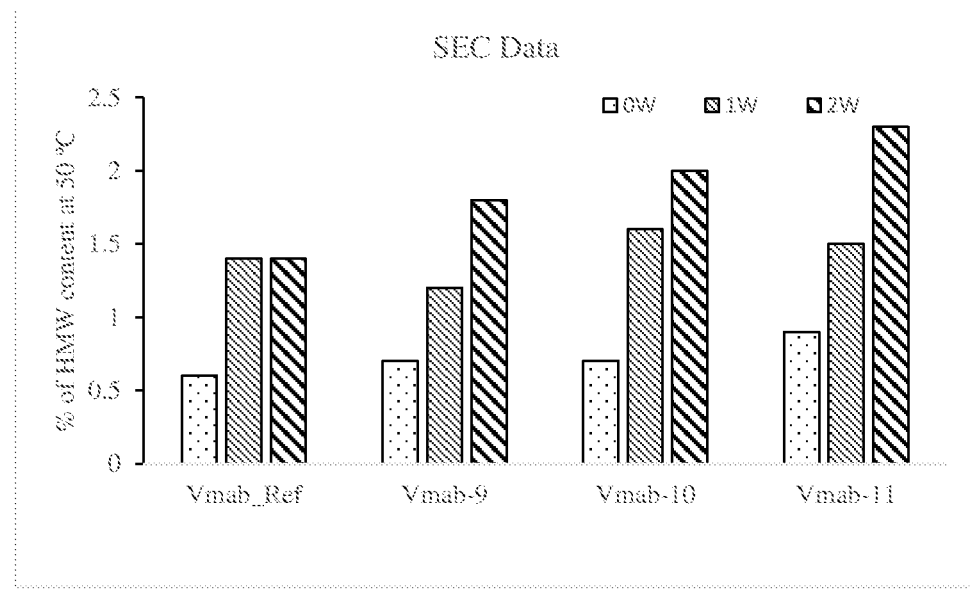
Figure 7:
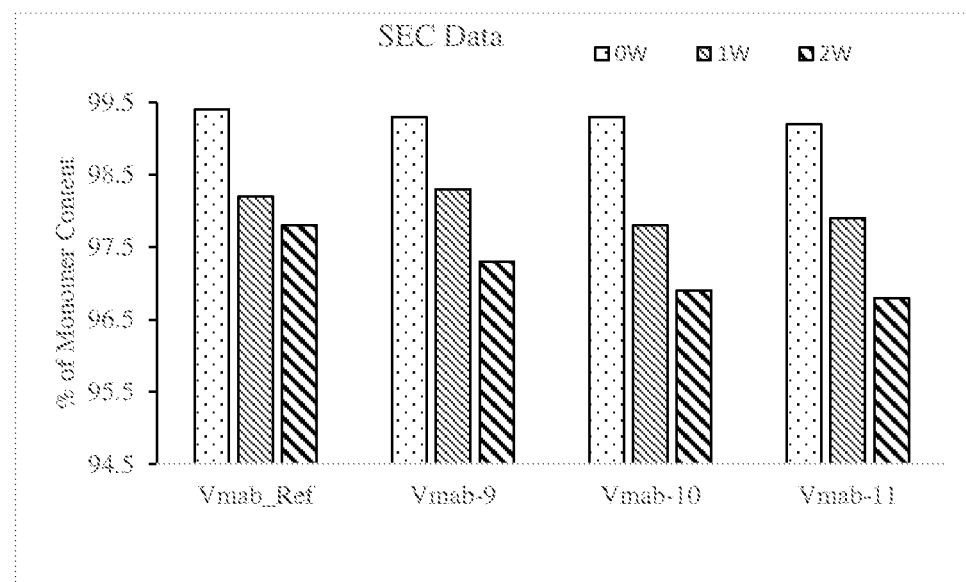
Figure 8:
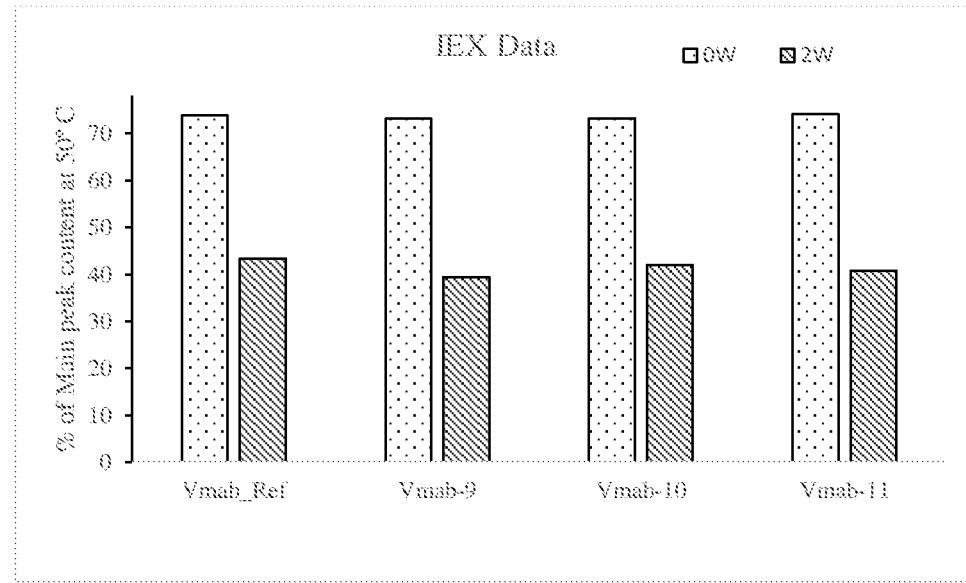
FIG. 8 illustrates the effect of buffer on the main peak content vedolizumab (60 mg/ml) formulations prepared as per example 4 and analyzed using IEX chromatography, after two weeks at 50° C.

From the above experiments, optimum concentration of excipients were selected for vedolizumab and was formulated in various buffer background with the same composition. Details of the formulations are given in Table 7. All the samples were subjected for accelerated stability studies at 50° C. for 2 weeks. Post which, the samples were analyzed for low molecular weight (LMW/fragments) species, high molecular weight species (HMW/aggregates) and monomer content [results are shown in FIG. 7(a)-(c)] using size exclusion chromatography (SEC) and also checked for main peak content, using ion exchange chromatography content [results are shown in FIG. 8]. Visual inspection data of the vedolizumab samples are given in Table 8.

TABLE 7

Compositions of vedolizumab formulations in different buffer background.

| Sample Name | Composition |
|---|---|
| Vmab_ref | Vedolizumab 60 mg/ml, 50 mM histidine buffer, monohydrochloride, 27.4 mg/mL L-arginine hydrochloride, 104.17 mg/mL sucrose, 0.6 mg/mL polysorbate 80 |
| Vmab-9 | Vedolizumab 60 mg/ml, 20 mM phosphate buffer, sucrose 60 mg/ml and 0.6 mg/ml polysorbate 80, 10.5 mg/ml arginine |
| Vmab-10 | Vedolizumab 60 mg/ml, 20 mM succinate buffer, sucrose 60 mg/ml and 0.6 mg/ml polysorbate 80, 10.5 mg/ml arginine |

TABLE 7-continued

Compositions of vedolizumab formulations in different buffer background.

| Sample Name | Composition |
|---|---|
| Vmab-11 | Vedolizumab 60 mg/ml, 20 mM acetate buffer, sucrose 60 mg/ml and 0.6 mg/ml polysorbate 80, 10.5 mg/ml arginine |

TABLE 8

Visual inspection data of vedolizumab (60 mg/ml) formulations prepared as per example 4

| Sample Name | Visual Inspection at 50° C. | | |
|---|---|---|---|
| | 0 W | 1 W | 2 W |
| Vmab_ref | Clear | Slightly Opalescent | Slightly Opalescent |
| Vmab-9 | Slightly Opalescent | Slightly Opalescent | Slightly Opalescent |
| Vmab-10 | Clear | Clear | Clear |
| Vmab-11 | Clear | Clear | Clear. |

W—indicates weeks

Liquid formulations of vedolizumab samples prepared as per example 1, 2, 3 and 4 were subjected for lyophilization technique known in the art and checked for stability.

Example 5

High Concentration Formulations of Vedolizumab

Vedolizumab at a concentration of 30 mg/ml in 40 mM histidine buffer background was obtained from downstream chromatographic steps were buffer exchanged into 40 mM histidine-phosphate buffer background with excipients (Vmab-12) and concentrated to 120 mg/ml where as in case of (Vmab 13 and 14) first vedolizumab was buffer exchanged into 40 mM histidine-phosphate buffer and then excipients were added followed by concentrating up to 120 mg/ml. Details of the formulations are given in Table 9. Post which the sample were stored at 2-8° C. for one week and, the samples were analyzed for low molecular weight (LMW/fragments) species, high molecular weight species (HMW/aggregates) and monomer content [results are represented in Table 10] using size exclusion chromatography (SEC) and also checked for main peak content, using ion exchange chromatography content [results are represented in Table 11]. Visual inspection data of the vedolizumab samples are given in Table 12.

TABLE 9

Compositions of high concentration of vedolizumab formulations prepared as per example 5.

| Sample Name | Composition |
|---|---|
| Vmab-12 | Vedolizumab 120 mg/ml, 40 mM Histidine-phosphate buffer, Trehalose 70 mg/ml and, 5.3 mg/ml arginine; pH 6.0 |
| Vmab-13 | Vedolizumab 120 mg/ml, 40 mM Histidine-phosphate buffer, and 5.3 mg/ml arginine; pH 6.0 |
| Vmab-14 | Vedolizumab 120 mg/ml, 40 mM Histidine-phosphate buffer, Trehalose 70 mg/ml and, 5.3 mg/ml arginine; pH 6.0 |

TABLE 10

SEC data of vedolizumab formulation prepared as per example 5.

| Sample Name | % of HMW at 2-8° C. | | % of monomer at 2-8° C. | |
|---|---|---|---|---|
| | 0 W | 1 W | 0 W | 1 W |
| Vmab-12 | 0.2 | 0.1 | 99.8 | 99.9 |
| Vmab-13 | 0.2 | 0.1 | 99.8 | 99.9 |
| Vmab-14 | 0.2 | 0.1 | 99.8 | 99.9 |

W—indicates weeks

TABLE 11

IEX data of vedolizumab formulation prepared as per example 5.

| Sample Name | % Acidic variants at 2-8° C. | | % main peak content at 2-8° C. | | % of basic variants at 2-8° C. | |
|---|---|---|---|---|---|---|
| | 0 W | 1 W | 0 W | 1 W | 0 W | 1 W |
| Vmab-12 | 25.9 | 23.74 | 68.2 | 68.8 | 5.9 | 7.5 |
| Vmab-13 | 25.4 | 22.2 | 68.8 | 70.8 | 5.8 | 7.0 |
| Vmab-14 | 25.9 | 26.36 | 68.4 | 67.1 | 5.7 | 6.6 |

W—indicates weeks

TABLE 12

Visual inspection data of vedolizumab formulations prepared as per example 5.

| Sample Name | Visual inspection at 2-8° C. | |
|---|---|---|
| | 0 W | 1 W |
| Vmab-12 | Clear | Clear to Slight Opalescence |
| Vmab-13 | Clear | Slight Opalescence |
| Vmab-14 | Clear | Opalescence |

W—indicates weeks

Example 6

Formulations of Vedolizumab in the Presence of Sugar, Salt and Amino Acid

To understand the cumulative stability effect of combinations of various excipients such as salt, sugar, and amino acid, vedolizumab in histidine buffer background was buffer exchanged to histidine-phosphate buffer containing various excipients. Details of the formulations are given in Table 13. All the samples were subjected for accelerated stability studies at 40° C. for 4 weeks. Post which, the samples were analyzed for high molecular weight species (HMW/aggregates) and monomer content [results are represented in Table 14] using size exclusion chromatography (SEC) and also checked for main peak content, using ion exchange chromatography content [results are represented in Table 15]. Visual inspection data of the vedolizumab samples are given in Table 16. Further, the samples were also checked for change in pH (Table 17) viz., for stability of pH.

TABLE 13

Compositions of vedolizumab formulations prepared as per example 6.

| Sample Name | Composition |
|---|---|
| Vmab-Ref | Vedolizumab 60 mg/ml, 50 mM histidine buffer, monohydrochloride, 27.4 mg/mL L-arginine hydrochloride, 104.17 mg/mL sucrose, 0.6 mg/mL polysorbate 80; pH 6.0 |
| Vmab-15 | Vedolizumab 60 mg/ml, 40-mM histidine-phosphate buffer, Sucrose 60 mg/mL, Arginine•HCl 5.3 mg/mL, NaCl-2.92 mg/mL, polysorbate 80-0.6 mg/mL; pH 6.0 |
| Vmab-16 | Vedolizumab 60 mg/ml, 40-mM histidine-phosphate buffer, Trehalose 70 mg/mL, Arginine•HCl 5.3 mg/mL, NaCl-2.92 mg/mL, polysorbate 80-0.6 mg/mL; pH 6.0 |
| Vmab-17 | Vedolizumab 60 mg/ml, 20-mM histidine-phosphate buffer, Trehalose 60 mg/mL, Arginine•HCl 5.3 mg/mL, Glycine-1 mg/mL, polysorbate 80-0.6 mg/mL; pH 6.0 |
| Vmab-18 | Vedolizumab 60 mg/ml, 20-mM histidine-phosphate buffer, Trehalose 70 mg/mL, Arginine•HCl 5.3 mg/mL, Glycine-1 mg/mL, NaCl-2.92 mg/mL, polysorbate 80-0.6 mg/mL; pH 6.0 |

TABLE 14

SEC data of vedolizumab formulation prepared as per example 6.

| Sample Name | % of HMW at 40° C. | | | | % of monomer at 40° C. | | | |
|---|---|---|---|---|---|---|---|---|
| | 0 W | 1 W | 2 W | 4 W | 0 W | 1 W | 2 W | 4 W |
| Vmab-Ref | 1.8 | 2.2 | 3.0 | 2.6 | 98.2 | 97.6 | 96.9 | 96.8 |
| Vmab-15 | 2.5 | 2.3 | 1.6 | 2.3 | 96.8 | 97.7 | 97.8 | 97.3 |
| Vmab-16 | 2.9 | 3.4 | 3.5 | 4.4 | 97.0 | 96.5 | 96.3 | 95.1 |
| Vmab-17 | 2.9 | 3.3 | 4.0 | 5.2 | 97.0 | 96.5 | 95.7 | 94.0 |
| Vmab-18 | 3.0 | 3.5 | 4.0 | 5.0 | 97.0 | 96.3 | 95.6 | 94.2 |

W—indicates weeks

TABLE 15

IEX data of vedolizumab formulation prepared as per example 6.

| Sample Name | % Acidic variants at 40° C. | | | | % of main peak content at 40° C. | | | | % of basic variants at 40° C. | | | |
|---|---|---|---|---|---|---|---|---|---|---|---|---|
| | 0 W | 1 W | 2 W | 4 W | 0 W | 1 W | 2 W | 4 W | 0 W | 1 W | 2 W | 4 W |
| Vmab-Ref | 20.1 | 22.6 | 25.2 | 52.4 | 72.9 | 59.0 | 55.8 | 35.3 | 7.1 | 18.4 | 19.0 | 12.4 |
| Vmab-15 | 20.2 | 20.1 | 20.1 | 23.3 | 72.4 | 51.0 | 46.1 | 25.1 | 6.9 | 27.1 | 27.4 | 28.6 |
| Vmab-16 | 21.5 | 20.1 | 20.1 | 20.4 | 72.0 | 49.6 | 44.7 | 31.9 | 6.5 | 30.4 | 32.6 | 25.9 |
| Vmab-17 | 21.7 | 19.0 | 24.4 | 39.0 | 72.1 | 54.1 | 45.5 | 33.7 | 6.2 | 26.9 | 30.1 | 27.3 |
| Vmab-18 | 22.1 | 20.3 | 23.1 | 39.1 | 69.6 | 49.9 | 43.3 | 32.1 | 8.3 | 29.8 | 33.7 | 28.8 |

W—indicates weeks

TABLE 16

Visual inspection data of vedolizumab formulations prepared as per example 6.

| Sample Name | Visual Inspection at 40 | | | |
|---|---|---|---|---|
| | 0 W | 1 W | 2 W | 4 W |
| Vmab-Ref | Clear | Slightly opalescent | Slightly opalescent | Clear with tiny particles |
| Vmab-15 | Clear | Opalescent | Opalescent | Opalescent |
| Vmab-16 | Clear | Clear | Clear | Clear with few particles |
| Vmab-17 | Clear | Clear | Clear | Clear with tiny particles |
| Vmab-18 | Clear | Clear | Clear | Clear with few tiny particles |

W—indicates weeks

TABLE 17 pH values of vedolizumab formulations observed over a period of time (0 week to 4 weeks), when stored at 40° C.

| Sample Name | pH at 40° C. | | | |
|---|---|---|---|---|
| | 0 W | 1 W | 2 W | 4 W |
| Vmab-Ref | 6.19 | 6.19 | 6.31 | 6.39 |
| Vmab-15 | 6.16 | 6.36 | 6.37 | 5.48 |
| Vmab-16 | 6.14 | 6.17 | 6.18 | 6.12 |
| Vmab-17 | 6.18 | 6.20 | 6.21 | 6.13 |
| Vmab-18 | 6.12 | 6.14 | 6.16 | 6.13 |

W—indicates weeks

The invention claimed is:

1. A pharmaceutical formulation of an α4β7 antibody comprising vedolizumab antibody, buffer having pH of 6.0 to 7.0, sugar free amino acid, salt and surfactant, wherein the concentration of sugar is less than 80 mg/ml and concentration of amino acid is less than 15 mg/ml.

2. The pharmaceutical formulation of vedolizumab antibody according to claim 1, wherein the buffer is phosphate buffer or histidine-phosphate buffer.

3. The antibody formulation according to claim 2, wherein the sugar is trehalose or sucrose.

4. The pharmaceutical formulation of vedolizumab antibody according to claim 1, wherein the formulation is stable at 40° C. for two weeks and maintains at least 95% of the monomeric content of the antibody under above mentioned storage conditions.

5. The antibody formulation according to claim 1, wherein the concentration of the antibody is from about 50 mg/ml to 200 mg/ml.

6. The antibody formulation according to claim 1, wherein the free amino acid is arginine, or lysine, or glycine or combination thereof.

* * * * *